United States Patent [19]

Yamashina

[11] Patent Number: 5,194,385
[45] Date of Patent: Mar. 16, 1993

[54] HYBRIDOMA AND MONOCLONAL ANTIBODY MLS102 WHICH RECOGNIZES A NEUACα2→6GALNAC SUGAR CHAIN PRESENT ON HUMAN INTESTINAL CANCER CELLS

[75] Inventor: Ikuo Yamashina, Kyoto, Japan
[73] Assignee: Shionogi & Co., Ltd., Osaka, Japan
[21] Appl. No.: 613,943
[22] Filed: Nov. 13, 1990

Related U.S. Application Data

[63] Continuation of Ser. No. 75,847, Jul. 20, 1987, abandoned.

[30] Foreign Application Priority Data

Jul. 29, 1986 [JP] Japan .............................. 61-179757

[51] Int. Cl.$^5$ .................. C12N 5/20; C12N 15/02; C07K 15/28; C12P 21/08
[52] U.S. Cl. .................. 435/240.27; 530/387.5; 530/388.8; 435/70.21; 435/172.2
[58] Field of Search .................. 530/387, 387.5, 388.8; 435/240.27, 70.21, 172.2

[56] References Cited

PUBLICATIONS

Johnson, V. G. et al. "Analysis of a Human Tumor-Associated Glycoprotein (TAG-72) Identified by Monoclonal Antibody B72.3", *Cancer Research* 46:850–857, Feb. 1986.
Colcher, D. et al. "A Spectrum of Monoclonal Antibodies Reactive with Human Mammary Tumor Cells," *Proc. Nat'l. Acad. Sci.* 78(5):3199–3203, May 1981.
Kurosaka, A. et al. "Mucin–Carbohydrate Directed Monoclonal Antibody," *FEBS Letters* 215(1):137–139, May 1987.
Nudelman, E. et al. "Novel Fucolipids of Human Adenocarcinoma. Disialosyl Le$^a$Antigen (III$^4$Fuc III$^{6-}$NeuAcIV$^3$NeuAcLc$_4$) of Human Colonic Adenocarcinoma and the Monoclonal Antibody (FH7) Defining This Structure," *J. Biol. Chem.* 261(12):5487–5495, Apr. 25, 1986.
Gottschalk, A. et al. "Submaxillary Gland Glycoproteins," In: *Glycoproteins*, Gottschalk, A. (ed.), Elsevier, Amsterdam, New York, 1972, pp. 810–829.
Kannagi et al. in Weir et al. Eds. "Handbook of Exptl. Immunol." vol. 4, Blackwell Sci Publ., May 30, 1986.
Giraldo et al, "From Oncogenes to Tumor Antigens" Elsevier Sci. Publ. 1985.
Kurosaka et al., *J. Biol. Chem* 263:8724–8776, 1988.
*The Journal of Biological Chemistry*, Nakada et al., vol. 266, No. 19, pp. 12402–12405, 1991.

Primary Examiner—David L. Lacey
Assistant Examiner—Paula Hutzell
Attorney, Agent, or Firm—Birch, Stewart, Kolasch & Birch

[57] ABSTRACT

The present invention relates to a monoclonal antibody MLS 102 recognizing human intestinal cancer cells, especially their sugar chain of glycoprotein, and more specifically NeuAc α2→6GalNAc. The invention also relates to a hybridoma producing the monoclonal antibody which is prepared by fusing splenic cells of a mouse immunized by human intestinal cancer cells with myeloma cells.

2 Claims, 2 Drawing Sheets

HYBRIDOMA AND MONOCLONAL ANTIBODY MLS102 WHICH RECOGNIZES A NEUACα2→6GALNAC SUGAR CHAIN PRESENT ON HUMAN INTESTINAL CANCER CELLS

This application is a continuation of application Ser. No. 07/075,847 filed on Jul. 20, 1987, now abandoned.

BACKGROUND OF THE INVENTION

1. Field of the Invention

The present invention relates to a monoclonal antibody MLS 102 specifically recognizing a cancer-associated sugar chain antigen and to a hybridoma producing it. More specifically, this invention pertains to a monoclonal antibody MLS 102 which binds specifically to cancer cell derived from human intestinal cancer tissue, in which MLS 102 binds to a sialic acid-containing sugar chain of glycoprotein but not to that of glycolipid; MLS 102 also binds to a sugar chain NeuAcα2→6GalNAc which is abundant in ovine or bovine submaxillary mucin. This invention also pertains to a hybridoma MLS 102 which stably grows in abdominal cavity of mouse and produces the monoclonal antibody MLS 102.

2. Description of the Prior Art

It has been recognized that on the surface of cells there are complex carbohydrates such as glycoprotein, glycolipid and proteoglycan, whose sugar chains are altered as normal cells are transformed into cancer cells. Elucidation of the mutation, that is, the change of sugar chain structure has been attempted mainly by chemically analyzing the sugar chain. However, it has become possible to obtain such a monoclonal antibody as specifically binding to a sugar chain changed on the surface of a cancer cell since 1975 when Köhler and Milstein established the method to make a hybridoma and obtain a monoclonal antibody therefrom. Recently, it has been reported that many of the monoclonal antibodies recognizing a cancer-associated antigen recognize a sugar chain and, therefore, the significance of a monoclonal antibody recognizing a cancer-associated sugar chain antigen has been pointed out and, further, some sugar chain structures of the cancer-associated antigens have been determined. It is believed that such monoclonal antibodies play a significant role in a clinical field such as a diagnosis, in an inspection of cancer therapy of cancer as well as in studies on cancer. Indeed, CA19-9, which is one type of cancer-associated sugar chain antigen, in sera of cancer patients can be assayed by using a monoclonal antibody NS19-9 specifically recognizing CA19-9 (J. Magnani et al., J. Biol. Chem. 257, 14365 (1982)), which has been effectively utilized in a diagnosis of pancreatic cancer.

Most of the conventional monoclonal antibodies bind to glycolipid on the surface of cancer cells since it is hard to prepare a monoclonal antibody binding to a sugar chain of glycoprotein. Moreover, the structures of the sugar chains recognized by the antibodies have been determined by using a glycolipid. However, it has been revealed that most of the cancer-associated sugar chain antigens appearing in sera of cancer patients are expressed on sugar chains of mucin-type glycoproteins because glycolipid is a minor component in sera. Therefore, a monoclonal antibody recognizing a sugar chain of glycoprotein has been desired as diagnostics of cancer used in a usual method employing sera.

SUMMARY

Monoclonal antibody MLS 102 is produced by a hybridoma which is selected, as one producing a monoclonal antibody binding to mucin-type glycopeptide prepared from LS180 (human intestinal cancer cell line, ATCC CL-187), from many hybridomas provided by fusing the splenic cell of immunized mouse with the myeloma cell. Namely, the monoclonal antibody MLS 102 of this invention recognizes human intestinal cancer cells and, specifically, sugar chains of glycoproteins which seemed hard to obtain in the prior art. More specifically, it recognizes NeuAcα2→6GalNAc, which is abundant in human intestinal cancer tissues and ovine and bovine submaxillary mucins.

DETAILED DESCRIPTION OF THE INVENTION

Figure 1:
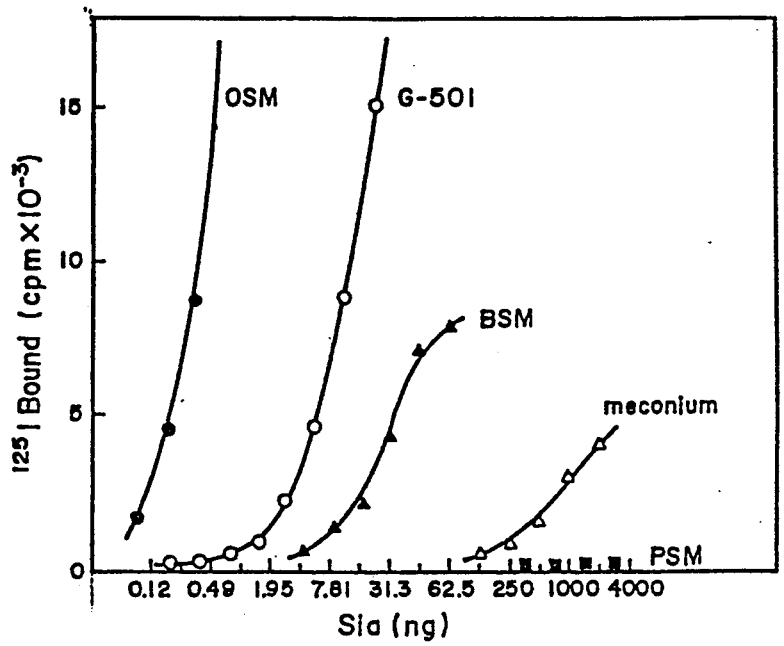
FIG. 1 shows an affinity of G-50I and glycoprotein of ovine, bovine and porcine submaxillary mucins (described as OSM, BSM and PSM) and meconium to MLS 102 bound to polystyrene beads. The ordinate means an amount of $^{125}$I-MLS 102 bound. The abscissa indicates an amount of a sample added as an amount of sialic acid.

Monoclonal antibody MLS 102 is produced by a hybridoma which is selected, as one producing a monoclonal antibody binding to mucin-type glycopeptide prepared from LS180 (ATCC CL-187), from many hybridomas provided by fusing the splenic cell of immunized mouse with the myeloma cell. Namely, one of the characteristics of this invention is that the monoclonal antibody of this invention binds to sugar chains of glycoproteins which seemed hard to obtain in the prior art.

The monoclonal antibody MLS 102 of this invention binds specifically to cancer cells but not to normal cells in human intestinal cancer tissue. Further, it binds to ovarian, gastric and esophageal cancer cells and may also bind to other human cancer cells.

The monoclonal antibody of the present invention does not bind to glycolipid, that is, it does not have any specificity to a crude glycolipid fraction extracted from bovine or porcine brain, LS180 cell, SW1116 cell (ATCC CCL233) or human meconium. It is well known that SW1116 cell is a cell line of human intestinal cancer and produces CA19-9 (J. Magnani et al., the same as mentioned above). Taking the above mentioned properties of this antibody into consideration, it can be said that the antibody of this invention has a specific affinity to sugar chain of glycoproteins. Most of the conventional monoclonal antibodies recognizing cancer-associated sugar chain antigen have an affinity to sugar chain of glycolipid. Therefore, the antibody of this invention can be regarded as a novel type of monoclonal antibody having different properties from conventional ones. Moreover, this antibody does not bind to glycolipid from SW1116 and so it is concluded that it is different from NS19-9.

The monoclonal antibody of this invention also has an affinity to glycoprotein in human meconium. It is well known that some of cancer-associated antigens are temporarily expressed in infancy and, therefore, they are called carcinoembryonic antigen. From the above aspect, the relationship between carcinogenesis and infancy has been remarked. Since the antibody of this invention binds to glycoprotein in meconium, it is concluded that the sugar chain antigen recognized by this antibody is expressed both in human intestinal cancer tissue and in human infant intestinal tissue.

The monoclonal antibody of this invention has an affinity to mucin type glycoprotein prepared from ovine, bovine or porcine submaxillary gland, too. Up to this time only two kinds of antigens, that is, Forssman antigen and H-D antigen are known as antigens which are expressed in other species of animal that is expressed in a human cancer. However, an antigen expressed in submaxillary mucin of other species of animal such as an antigen recognized by the antibody of this invention has not yet been known.

Further, it is revealed that the monoclonal antibody of this invention has an affinity to the sugar chain of the structure NeuAc$\alpha$2→6GalNAc. The higher the density of the sugar chain of the structure becomes, the more the affinity of the antibody increases. The sugar chain of the structure NeuAc$\alpha$2→6GalNAc recognized by the antibody is observed in normal human intestinal tissue in so small quantity that the antibody has low affinity to normal human intestinal tissue. On the contrary, the above chain of two sugars is frequently expressed and abundant in human intestinal cancer tissue, and, therefore, this antibody binds only to cancer tissue. These two sugars are main constituents of ovine and bovine submaxillary mucin and especially ovine submaxillary mucin contains them in a higher density. This agrees with the fact that the monoclonal antibody of this invention binds to ovine, bovine and porcine submaxillary mucins and in this order the affinity decreases.

A hybridoma producing the monoclonal antibody of this invention is prepared by fusing myeloma cell with splenic cell (prepared from mouse immunized by peritoneally inoculating human intestinal cancer cell LS180 thereinto according to the usual method) and selecting a clone which has an affinity to mucin-type glycopeptide isolated and purified from LS180 cell. The hybridoma can be stably stored in 10% dimethylsulfoxide and 90% fetal calf serum (FCS) in liquid nitrogen ($-198°$ C.) for a long time. As occasion demands, a part of the hybridoma may be thawed and incubated in RPMI-1640 or Dulbecco's MEM containing 20% FCS for its growth, and then the resultant is inoculated into the abdominal cavity of a mouse to which pristane (0.5 ml/mouse) has been administered 2 weeks to 3 months before to give a large amount of monoclonal antibody MLS 102 of this invention in the ascites 10 to 14 days after the inoculation of the hybridoma. In this method 7 to 14 mg of the monoclonal antibody can be stably prepared from about 5 ml of ascites per mouse. This monoclonal antibody in the ascites can be readily purified by applying it to an affinity column such as protein A-sepharose 4B after fractionation with ammonium sulfate and subsequent dialysis. Even in the case of incubating the hybridoma in a culture medium, the monoclonal antibody MLS 102 is secreted into the medium in a concentration of 20 to 40 $\mu$g/ml about 3 days after incubation and, therefore, it also can be recovered from the medium.

The hybridoma MLS 102 has been deposited with European Collection of Animal Cell Cultures (ECACC) and has an accession number of 86070307 under the Budapest Treaty which is dated Jul. 3, 1986. The address of the depository is ECACC, PHLS, CAMR, Porton Down, Salisbury, Wilts.

EXAMPLE

The following examples further describe but do not restrict this invention.

EXAMPLE 1

Preparation of Hybridoma

LS180 cell and Balb/c mouse are used as an antigen and a mouse to be immunized. Into Balb/c mouse 1 to $2\times10^6$ LS180 cells, which were incubated in Eagle medium containing 10% FCS, suspended in 0.5 ml of physiological saline are peritoneally administered 9 times in 3 months. Next, 1 to $2\times10^6$ LS180 cells in 0.5 ml of physiological saline are intravenously administered into the mouse to obtain splenic cells from the mouse 3 days after the administration. The splenic cells ($1.5\times10^8$) and myeloma cells ($2\times10^7$, sp2/O-Ag14) are mixed in Dulbecco's medium without FCS and centrifuged at 1,000 r.p.m. for 5 min for washing. A solution (0.5 ml) containing 35% polyethyleneglycol (PEG) #1000 is mixed with the Dulbecco's medium with FCS. The resulting mixture is centrifuged at 1,000 r.p.m. for ca. 5 min to fuse the splenic cells with the myeloma cells. The PEG used for the fusing is diluted with 5 ml of Dulbecco's medium without FCS and 5 ml of Dulbecco's medium with 20% FCS and removed by centrifuging at 1,000 r.p.m. for 5 min. The cells without PEG are suspended in 50 ml of HT medium comprising 72% Dulbecco's medium and 8% NCTC 109 medium, 1 drop (c.a. 0.1 ml) of which is placed in each well of 96 well tissue culture plate and incubated for 24 hr. Then, 1 drop of HT medium containing 0.8 $\mu$M aminopterine is added to each well to change the medium to HAT medium. Hybridomas prepared by the fusing are selected from not fused splenic cells and myeloma cells by an incubation in HAT medium. About 10 days after the fusing the supernatant of each well is collected and assayed to determine if it has an affinity to G-50I (see Referential example) adsorbed on a well according to the method shown in Example 4. The clones showing an affinity to the G-50I are further applied twice to the cloning by the dilution method to give several kinds of hybridomas. Monoclonal antibodies produced by these hybridomas were assayed on an affinity to human intestinal cancer tissue, one of which, namely MLS 102, showed the specific affinity to the cancer cell.

EXAMPLE 2

Preparation and Purification of Monoclonal Antibody

To Balb/c mouse is peritoneally administered 0.5 ml of pristane. The hybridoma, which produces MLS 102, is incubated in a hybridoma growth medium comprising 10% Dulbecco's medium, 10% NCTC 109 medium and 20% FCS, $10^7$ cells of which are suspended in 0.5 ml of Hanks' solution and peritoneally administered to the above mouse about 1 month after the administration of pristane. About 10 days after the ascites are recovered from the mouse. Each mouse had about 5 to 7 ml of ascites containing about 10 mg of MLS 102. Ammonium sulfate is added to the ascites to bring it to 50% saturation. The mixture is centrifuged and the precipitate is dissolved in 0.1M borate buffer solution containing 0.14M sodium chloride (pH 8.2, Buffer A) and dialyzed against the same buffer. The resultant is divided into several portions, which are applied to a protein A-Sepharose CL-4B column and washed with Buffer A. The column is previously equilibrated with Buffer A and contains 6 ml of a resin. This column can adsorb about 30 mg of IgG. The antibody bound to the column is eluted with 0.1M acetic acid containing 0.15M sodium chloride. The eluate is neutralized with 1M Tris. To the eluate is added ammonium sulfate to bring it to 50% saturation. After centrifugation the precipitate is dissolved in Buffer A and dialyzed against Buffer A to give the monoclonal antibody MLS 102.

EXAMPLE 3

Affinity of Monoclonal Antibody MLS 102 to Human Intestinal Cancer Tissue

Human intestinal cancer tissue fixed with formalin is dehydrated and fixed with paraffin. Thin slices are prepared from the tissue and the paraffin is removed with xylene from the slice. The xylene is washed out with alcohol. Finally, the slice is washed with phosphate buffered saline (PBS) and soaked in PBS. The monoclonal antibody MLS 102 is allowed to bind to the slice overnight. The slice is washed and allowed to react with antimouse IgG antibody labelled with Fluorescein isothiocyanate, FITC. After washing out the unbound FITC-IgG, the slice is observed under a fluorescence microscope. As a result, MLS 102 does not bind to normal tissue at all and specifically binds to mucin-like substance secreted by cancer cells. The result shows that MLS 102 recognizes a cancer-associated antigen.

EXAMPLE 4

Affinity of Monoclonal Antibody MLS 102 to Mucin-Type Glycopeptide

To the poly(vinyl chloride)-well coated with mucin-type glycopeptide (G50-I) prepared from human intestinal cancer cell LS180 through polylysine and glutaraldehyde is added 1% bovine serum albumin and allowed to stand for 1 hr. After washing, monoclonal antibody MLS 102 is added to the well and allowed to react overnight. After washing the well, $^{125}$I-labelled protein A is added to the well and allowed to react for 2 hr, followed by washing the well. An affinity of MLS 102 to G-50I is assayed by measuring the radioactivity of $^{125}$I bound to the well. As a result it was revealed that MLS 102 binds to G-50I. The same experiment was done by using G-50I from which sialic acid was removed and MLS 102 had no affinity to such G-50I. It means that MLS 102 binds to sugar chain containing sialic acid of mucin-type glycopeptide.

An affinity of MLS 102 may be assayed by using polystyrene beads immobilizing MLS 102. Polystyrene beads (EP-03, #80, Sekisui Chemical Co., Ltd.) are washed with phosphate buffered saline (PBS, pH 7.4) containing 0.15M sodium chloride. The beads are allowed to stand in PBS containing 0.1 mg/ml of MLS 102 at 4° C. overnight and coated with the antibody. The beads are washed 3 times with PBS containing 5% bovine serum albumin (BSA), soaked in the same solution and allowed to stand for 1 hr. After removing the solution by vacuum, 100 μl of sample solution (containing G-50I), 50 μl of PBS containing 0.2% Tween 20 and 50 μl of PBS containing $^{125}$I-MLS 102 (12.5 ng) and 0.1% BSA (c.a. 200,000 counts) are well mixed with the beads and allowed to stand at 4° C. overnight, followed by washing the beads 3 times with PBS. The radioactivity bound to the beads is measured by a γ-counter to calculate the affinity to the antibody (FIG. 1).

EXAMPLE 5

Affinity of Monoclonal Antibody to Ovine, Bovine or Porcine Submaxillary Mucin

Mucin prepared from ovine, bovine or porcine submaxillary gland is allowed to react with polystyrene beads coated with MLS 102 according to the method of Example 4 to assay an affinity of MLS 102 to these materials. Aa a result, it is revealed that MLS 102 binds to ovine, bovine and porcine mucin and in this order the affinity decreases (FIG. 1 and Table 1).

Figure 2:
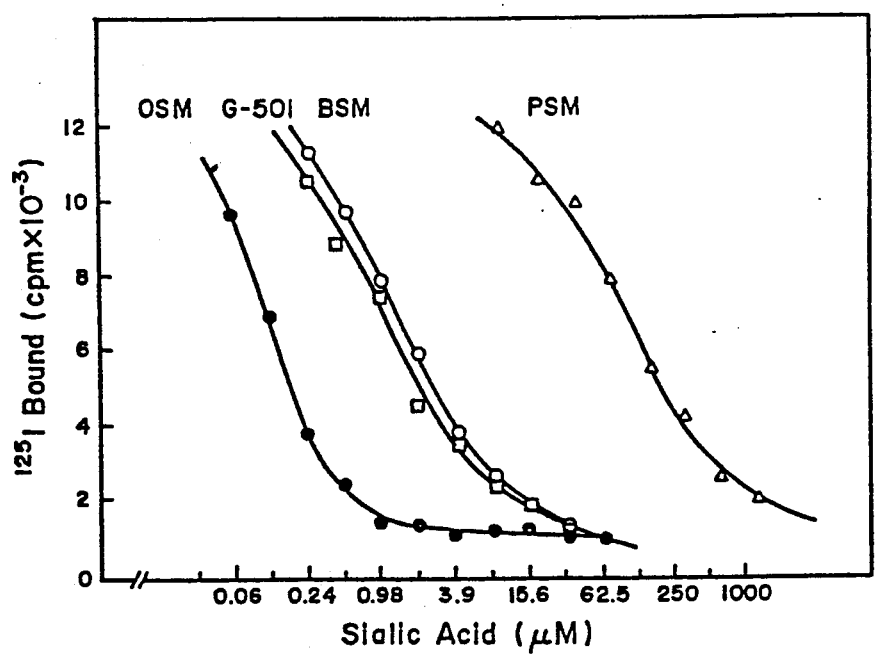
FIG. 2 shows an activity of OSM, BSM, PSM and G-50I to inhibit the binding of MLS 102 to G-50I. The ordinate means an amount of $^{125}$I-protein A bound. The abscissa indicates an amount of mucin added as an amount of sialic acid.

To each poly(vinyl chloride)-well coated with G-50I are added monoclonal antibody MLS 102 and submaxillary mucin of varying concentrations and allowed to stand overnight. According to the method of Example 4 an affinity of the antibody to G-50I is assayed by measuring an affinity of $^{125}$I-labelled protein A. Similar to the result of the above assay using beads, ovine, bovine and porcine submaxillary mucins inhibit the binding of the antibody to G-50I and in this order the activity decreases (FIG. 2). This means that the antibody binds to ovine, bovine and porcine submaxillary and mucins in this order the affinity decreases.

EXAMPLE 6

Affinity of Monoclonal Antibody MLS 102 to Glycoprotein in Meconium

In 10 ml of water is suspended 1.9 g of meconium and then 90 ml of a mixture of chloroform/methanol (2:1, V/V) is added thereto, stirred well and allowed to stand to give an organic phase (under layer) and an aqueous phase (upper layer). The upper layer is dried and extracted 3 times with a chloroform/methanol mixture (2:1 V/V). The extract and the under layer as noted above are combined to give a fraction of glycolipid in meconium, which is dried to be used in the following Example 7. To the residue of the extraction is added water and the mixture is stirred and centrifuged for removing insoluble materials to give the supernatant as a glycoprotein fraction of meconium. An affinity of MLS 102 to this glycopeptide fraction is assayed by using polystyrene beads as noted above and it is revealed that MLS 102 binds to this glycoprotein (FIG. 1).

EXAMPLE 7

Affinity of Monoclonal Antibody MLS 102 to Colostrum, Semen, Cord Blood, Saliva and Amniotic Fluid Every sample as captioned was prepared from a normal human. An affinity of MLS 102 to each sample is assayed by the method using polystyrene beads as noted in Example 4. As a result, MLS 102 did not bind to any samples (Table 1).

EXAMPLE 8

Affinity of Monoclonal Antibody MLS 102 to Glycolipid of Bovine or Porcine Brain, LS180 Cell and Meconium A bovine or a porcine brain and LS180 cells each is homogenized in water at 4° C. in a Dounce homogenizer. To the homogenate is added methanol and chloroform is such a way that the final ratio of chloroform:methanol:water becomes 2.7:5.4:2 (V/V). The mixture is stirred at room temperature for 30 min for extracting glycolipids. After centrifugation, to the precipitate is added 2 volumes of water and the mixture is homogenized. Then, 8 volumes of a mixture of chlorform/methanol (1:2, V/V) is added thereto to extract glycolipid with stirring, followed by centrifuging to give the extract. After the resulting two extracts are filtered through sellaite 535 and the filtrates are combined in a separatory funnel, to which water is added in such a way that the ratio of chloroform:methanol:water becomes 1:2:2.4 (V/V). After gently stirring and allowing to stand, the upper layer is removed and the lower layer is well mixed with 3 volumes of methanol. Then, 2 volumes of 0.001M potassium chloride is added thereto, gently stirred and allowed to stand overnight to give an upper layer. To a mixture of this upper layer and the upper layer as mentioned above is added isobutanol and dried under reduced pressure. The dried preparation in a mixture of chloroform/methanol/water (60:30:4.5, V/V) is stirred overnight and centrifuged for removing insoluble materials and the resulting supernatant is dried. The dried preparation is dissolved in a small quantity of water and dialyzed against water. After drying, the dried preparation is dissolved in methanol and centrifuged for removing insoluble materials to give a supernatant as a glycolipid fraction.

A glycolipid fraction of meconium was prepared in Example 6.

To each glycolipid fraction is added methanol in such a way that glycolipid in 1 mg (wet weight) of a starting material is dissolved in 20 μl of methanol. To a poly(vinyl chloride)-well is added 20 μl of the methanol solution. The methanol is evaporated under reduced pressure to coat the glycolipid on the surface of the well. To the well is added 1% bovine serum albumin and incubated for 30 min. After washing the well, monoclonal antibody MLS 102 is added thereto and allowed to react at room temperature for 3 hr. After washing the well, $^{125}$I-protein A is added thereto and allowed to react for 2 hr. After washing the well, the affinity of MLS 102 is assayed by measuring the radioactivity bound to the well. MLS 102 did not bind to any glycolipid fractions (Table 1).

EXAMPLE 9

Structure of Sugar Chain Recognized by Monoclonal Antibody MLS 102

A structure of the sugar chain recognized by MLS 102 is investigated by using ovine submaxillary mucin which has the highest affinity to MLS 102. A solution of a dried preparation of the mucin in anhydrous hydrazine is allowed to react at 100° C. for 9 hr. By this treatment the linkage between sugar and peptide in the mucin is cleaved and the sugar chain is isolated as a reducing sugar. The sugar chain is gel-filtrated through sephadex G-25. The affinity of MLS 102 to each fraction is assayed by measuring the activity of each fraction to inhibit the binding of MLS 102 to a well coated with bovine submaxillary mucin. The fraction containing the main sugar chains was identical with the fraction having an affinity to MLS 102. When the sugar chain is further applied to several types of filter paper chromatography and high-voltage filter paper electrophoresis, the same results were observed.

An inhibition test was done by using the main glycopeptide of ovine submaxillary mucin, NeuAcα2→6GalNAcα→Ser, and its isomer, NeuAcα2→6GalNAcβ→Ser, both of are artificially synthesized. As a result, both had the same affinity to the antibody and, therefore, it was concluded that MLS 102 has an affinity to NeuAcα2→6GalNAc, which is a main sugar chain of ovine submaxillary mucin.

Figure 3:
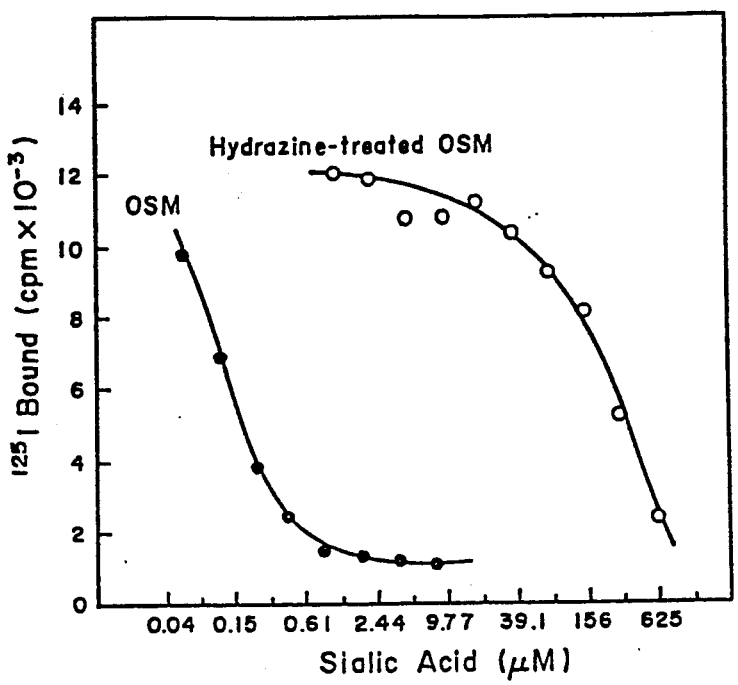
FIG. 3 shows the activity of OSM and sugar chain prepared form OSM by hydrazine decomposition to inhibit the binding of MLS 102 to G-50I. What are meant by the ordinate and the abscissa are the same as in FIG. 1.

When a sugar chain of ovine submaxillary mucin is isolated therefrom by hydrazine degradation, the inhibitory activity is dramatically reduced. It is inferred from the result that the affinity of MLS 102 deeply depends upon the density of the disaccharide NeuAcα2→6GalNAc on the polypeptide (FIG. 3).

TABLE 1

| Sample | Affinity of MLS 102 Affinity |
|---|---|
| G-50I | + |
| Ovine submaxillary mucin | ++ |
| Bovine submaxillary mucin | + |
| Porcine submaxillary mucin | ± |
| Glycoprotein in meconium | + |
| Glycolipid of LS180 | − |
| Glycolipid of bovine brain | − |
| Glycolipid of porcine brain | − |
| Glycolipid of meconium | − |
| Colostrum | − |
| Semen | − |
| Cord blood | − |
| Saliva | − |
| Amniotic fluid | − |

REFERENTIAL EXAMPLE

Preparation of G-50I

G-50I is a glycopeptide derived from a mucin-type glycoprotein produced by a human intestinal cancer cell line LS180 (ATCC CL-187) and is prepared according to the following method.

Figure 4:
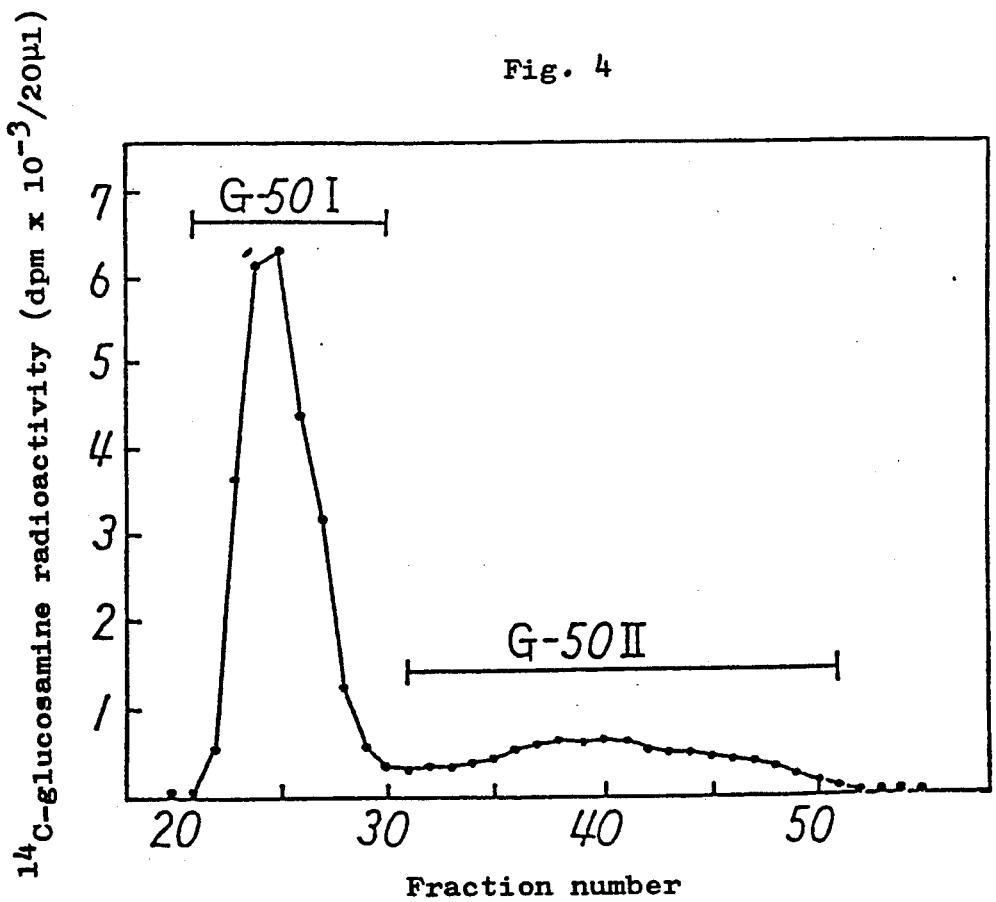
FIG. 4 shows the relation between the number of a fraction and [$^{14}$C] glucosamine radioactivity (dpm×10$^{-3}$/20 μl).

Human intestinal cancer cell line LS180 (ATCC CL-187) is incubated in Dulbecco's medium containing 10% fetal calf serum for 7 days and recovered. The collected cells are repeatedly washed with phosphate buffered saline (PBS, 137 mM sodium chloride, 2.7 mM potassium chloride, 8.1 mM disodium hydrogenphosphate, 1.5 mM potassium dihydrogenphosphate, 1.0 mM calcium chloride and 0.5 mM magnesium chloride). Then, PBS containing 1% Triton X-100 (Rohm & Haas) is added thereto and the mixture is stirred under ice-cooling. After centrifugation, the supernatant is dialyzed and freeze-dried. The resultant is defatted with chloroform/methanol (2:1) and suspended in acetate buffer containing 0.01M calcium acetate. Then, 1/50 parts of Pronase P (Kaken Pharmaceutical Co., Ltd.) to the above dried preparation is added thereto, followed by adding a small amount of toluene. The mixture is allowed to stand at 37° C. for 3 days for sufficient digestion of protein. To the solution which becomes almost clear is added the same volume of 10% trichloroacetic acid. After stirring, the mixture is allowed to stand and centrifuged for removing insoluble materials. The supernatant is well mixed with the same volume of ether and centrifuged. The supernatant is removed and to the lower layer (aqueous phase) is further added ether. The centrifugation is repeated 3 times. After it is confirmed that the aqueous phase becomes pH 5, it is applied to a column (1.3×60 cm) of sephadex G-25 pre-equilibrated with 0.5M pyridine-acetate buffer (pH 5.0) and developed with the same buffer. The eluate is collected by means of a fraction collector and the fractions positive in the orcinol-sulfuric acid reaction are combined and freeze-dried. The resulting dried powder is dissolved in 0.5M pyridine-acetate buffer (pH 5.0), gel-filtrated by a column of sephadex G-50 and fractionated into 5 ml portions by means of a fraction collector to give fractions (G-50I) passing through the G-50 column. These fractions usually contain glycopeptide derived from glycoprotein of mucin-type (0-glycoside type). FIG. 4 shows the relation between the number of a fraction and [$^{14}$C] glucosamine radioactivity (dpm×10$^{-3}$/20 μl).

The fractions 20-29 are combined and lyophilized to remove the solvent. The resulting powder is treated in the same manner as described above except for using sephadex G-200 to give practically pure mucin-type glycopeptide G-50I.

As explained in the above description of the invention, the monoclonal antibody MLS 102 enables us to make a precise decision in the diagnosis of various cancer, especially intestinal cancers. Further it becomes possible to provide the monoclonal antibody whenever it is necessary since the hybridoma producing the antibody can be preserved for a long period of time and proliferate stably in an abdominal cavity of mouse. Therefore, the monoclonal antibody MLS 102 and the hybridoma producing it bring an excellent effect to the diagnosis and therapy of cancer.

What we claim is:

1. A hybridoma having the designation MLS 102 (ECACC 86070307).

2. A monoclonal antibody MLS 102 produced by hybridoma MLS 102 (ECACC 86070307).

* * * * *